United States Patent [19]

Pacheco et al.

[11] Patent Number: 5,328,615

[45] Date of Patent: Jul. 12, 1994

[54] ALKYL CARBONATE RECOVERY PROCESS

[75] Inventors: Michael A. Pacheco, Naperville, Ill.; Franklin D. Darrington, Munster, Ind.

[73] Assignee: Amoco Corporation, Chicago, Ill.

[21] Appl. No.: 10,774

[22] Filed: Jan. 29, 1993

[51] Int. Cl.$^5$ .............................................. B01D 11/04
[52] U.S. Cl. ................... 210/634; 210/195.1; 210/511
[58] Field of Search ............... 210/634, 511, 195.1, 210/197

[56] References Cited

U.S. PATENT DOCUMENTS

5,214,185  5/1993  Nishihira et al. .................... 558/277

Primary Examiner—Frank Spear
Attorney, Agent, or Firm—Thomas A. Yassen; Richard A. Kretchmer

[57] ABSTRACT

A process is provided for separating alkyl carbonate from a feedstock comprising at least one alkyl carbonate and at least 0.01 percent by weight water comprising extracting the alkyl carbonate from the feedstock in a liquid-liquid extraction step comprising an extraction solvent selective for extracting alkyl carbonates relative to water in an amount sufficient to extract a substantial amount of the alkyl carbonates from the feedstock. The extraction solvent substantially comprises hydrocarbon boiling at a temperature ranging from about 50° F. to about 700° F. at atmospheric pressure and having a specific gravity ranging from about 0.50 to about 1.00.

20 Claims, 1 Drawing Sheet

ALKYL CARBONATE RECOVERY PROCESS

BACKGROUND OF THE INVENTION

This invention relates to a process for separating alkyl carbonate from feedstocks containing alkyl carbonate and water. More particularly, this invention relates to a liquid-liquid extraction process for separating alkyl carbonate from feedstocks comprising alkyl carbonate, water, and impurities such as unconverted alkanol from an alkyl carbonate production process for uses such as the production of high oxygen-content gasoline blending components (Oxygenates).

Oxygenates have been part of the United States gasoline strategy since the late 1970s. With the Clean Air Act Amendments of 1990, the demand for oxygenates is expected to increase even further. For example, starting in the winter months of 1992, gasoline containing 2.7 weight percent oxygen will have to be provided to approximately 40 metropolitan areas that have failed to meet carbon monoxide pollution standards. It is expected that in the near future, between 30 and 60 percent of the United States gasoline pool may be required to contain oxygenates.

The most commonly used oxygenates today are methanol, ethanol, and methyl tertiary butyl ether (MTBE). Although methanol and ethanol have high blending octanes, problems with toxicity, water miscibility, high Reid Vapor Pressure (RVP), high nitrogen oxide emissions, lower fuel efficiency, and cost have dampened industry enthusiasm for these components. Partially as a result of the above, MTBE has become particularly attractive.

Homologues of MTBE such as ethyl tertiary butyl ether (ETBE) and methyl tertiary amyl ether (TAME) are also gaining industry acceptance. Moreover, commercial activity with respect to ETBE and TAME is expected to increase relative to MTBE, in view of the recent Environmental Protection Agency decision to reduce the RVP requirements for gasolines well below 9 psia, the blending RVP of MTBE.

Oxygenate production capacity, however, is limited by ether plant capacity and by feedstock availability. MTBE and ETBE both utilize isobutylene as a feedstock while TAME uses isoamylene as a feedstock. Isobutylene and isoamylene are generally supplied to an ether facility in a petroleum refinery from a fluid catalytic cracking unit (FCC), a fluidized or delayed coker, or from downstream paraffin isomerization and dehydrogenation facilities. The availability of hydrocarbons having 4 carbons is limited by constraints such as, but not limited to, crude properties, FCC catalyst properties, FCC operating conditions, coking conditions, as well as other refinery operating constraints. The chemical mix of $C_4$ and $C_5$ paraffins, olefins, and aromatics as well as the particular mix of iso-olefins to normal olefins are similarly constrained.

Thus, there exists a great need in the petroleum industry for a low-cost method of increasing oxygenate production capacity that overcomes or avoids the obstacles described above.

The use of carbonates, and particularly the dialkyl carbonates in fuels has been the subject of several patents and patent applications.

European Patent Application Numbers 0 082 688 to Bretherick and 0 098 691 to Spencer disclose the use of dialkyl carbonate and dimethyl carbonate in fuels for use with spark ignition engines.

U.S. Pat. No. 4,380,455 to Smith discloses the use of dialkyl carbonates for preventing the phase separation of hydrous ethanol from liquid hydrocarbon fuel mixtures.

U.S. Pat. No. 4,891,049 to Dillon discloses the use of non-aromatic metals-free carbonates for reducing particulate emissions from distillate-based fuels such as diesel fuel and jet fuel.

Carbonates can be produced using any of several methods known in the art, each method having attendant advantages and penalties. Such methods include the carbonylation of alcohols, alkylene carbonate alcoholysis, urea alcoholysis, inorganic methods, and phosgene alcoholysis.

One of the oldest methods for manufacturing carbonates employs phosgene. The phosgene is generally contacted with methanol to form methyl chloroformate in accordance with the following reaction:

The methyl chloroformate reacts with an additional mole of methanol to form dimethyl carbonate as follows:

One associated penalty with the process described hereabove is that the process requires the use of toxic phosgene. Moreover, the method also leads to the co-production of other chloride-containing by-products such as alkyl chlorides, which can often be toxic themselves. Chlorine-containing by-products such as hydrogen chloride can also be particularly corrosive. Neutralization methods to balance the acidity of such chlorided components in order to mitigate such corrosive effects such as the addition of sodium hydroxide to drive the reaction by the production of sodium chloride and water, can be costly and can also compromise product quality.

Oxidative carbonylation is another method that has been used to produce carbonates. It is generally known that carbonates can be produced from alkanol and carbon monoxide in the presence of certain metal chlorides or metal alkoxy chlorides through an oxidation-reduction reaction. An example of such a reaction with methanol and carbon monoxide over a copper chloride catalyst is as follows:

Oxidation:

Reduction:

Overall:

U.S. Pat. No. 4,218,391 to Romano et al. discloses such a process for the production of carbonates comprising reacting an alkanol with oxygen and carbon monoxide in the presence of a catalyst consisting of a copper metal salt of the group of cuprous and cupric salts having a single inorganic anion.

U.S. Pat. No. 5,004,827 to Curnutt discloses a similar process for the production of carbonates comprising contacting an alkanol with carbon monoxide and oxygen in the presence of a heterogeneous catalyst comprising a metal halide such as cupric chloride with or without potassium chloride impregnated on an appropriate support such as activated carbon.

This reaction cannot generally be operated to high conversion because high concentrations of water in the reactor lead to low selectivity, i.e., high $CO_2$ yields. Additionally, excess water can lead to the formation of a variety of copper hydroxy chloride phases of the formula $Cu(Cl)_x(OH)_y \cdot nH_2O$. None of these phases are particularly effective for the production of carbonates.

For these, among other reasons, it is generally desirable that these reactions be conducted with a low conversion for each pass through the reactor with an effective strategy for feed/product separation and recycle of the unconverted feed.

Moreover, under typical oxidative carbonylation reaction conditions, the product stream generally comprises the alkyl carbonate, alkanol, and water, wherein the alkyl carbonate can form azeotropes with both the alkanol and water. For example, Table 1 illustrates the boiling point and composition of various binary azeotropes within a mixture comprising methanol, ethanol, dimethyl or diethyl carbonate, and water.

TABLE 1

| Boil. Pt.-Temp. °C. | Pure Comp. | Azeotrope Comp.- Wt % (@ 14.7 psia) |
|---|---|---|
| 62.7 | | 70% MeOH + 30% DMC |
| 65.0 | MeOH | |
| 74.0 | | 55% DMC + 45% EtOH |
| 77.5 | | 89% DMC + 11% $H_2O$ |
| 78.2 | | 96% EtOH + 4% $H_2O$ |
| 78.3 | EtOH | |
| 90.0 | DMC | |
| 91.0 | | 70% DEC + 30% $H_2O$ |
| 100.0 | $H_2O$ | |
| 126.0 | DEC | |

The formation of these various azeotropes complicates downstream separation steps such that they cannot be easily or effectively performed by conventional distillation methods.

Several methods have been suggested to overcome these product separation problems.

U.S. Pat. No. 3,963,586 to Ginnasi et al. discloses a process for separating dimethyl carbonate from a mixture of dimethyl carbonate, methyl alcohol, and water. In the disclosed process, water is fed to the top of an extraction distillation column at a water solvent to feed ratio by weight of at least 10:1. A stream of methyl alcohol and water with minor amounts of dimethyl carbonate is withdrawn from the bottom of the column while an overhead stream containing dimethyl carbonate, water, and a minor amount of methyl alcohol is directed overhead. The overhead product stream is generally cooled and decanted into a bottom organic phase containing dimethyl carbonate (97%) and water (3%) with a minor amount of methyl alcohol and a top aqueous phase containing a substantial amount of water (87%) with dimethyl carbonate (12%) and methyl alcohol (1%).

Such processes require extensive retrofitting and modifications in order to produce fuel blending components. For example, the organic phase containing 97% dimethyl carbonate and 3% water still generally requires desiccation or reprocessing in a water fractionation step or through other means to reduce the water content of the fuel sufficiently for fuels blending. Similarly, the aqueous phase containing 12% dimethyl carbonate must be undesirably reprocessed to the extraction distillation column along with the water component, at the expense of energy and capacity penalties. Moreover, processes that operate at a solvent to feed ratio by weight in excess of 10:1 can require distillation extraction columns having excessively large and thereby costly vessel diameters.

U.S. Pat. No. 4,162,200 to Himmele et al. discloses a process for obtaining dimethyl carbonate from its solutions in methanol by extractive distillation with an aprotic extractant at a column temperature profile ranging from 60° F. at the top of the column to 250° F. at the bottom. The methanol is generally carried upwards to the overhead product stream, leaving a bottoms product containing the dimethyl carbonate and aprotic extractant. The aprotic extractant is further characterized as:

(a) being substantially inert towards dimethyl carbonate, (b) boiling at a temperature above 100° C. at atmospheric pressure, (c) being miscible with dimethyl carbonate in all proportions, (d) having a dielectric constant, $\epsilon$, of from 4 to 90, and (e) having a dipole moment, $\mu$, of from 1.5 to 5 Debye.

The aprotic extractant is also added at the high extractant to dimethyl carbonate weight ratio of 0.5 to 50 kilograms of extractant per kilogram of dimethyl carbonate. The large volumes of aprotic extractants generally must be separated from the products and recovered at substantial expense to the refiner since these extractants can be costly and furthermore, can contaminate the finished product.

Moreover, processes requiring extractive distillation for alkyl carbonate separation such as those described above, generally require additional processing equipment such as reboilers, overhead condensers, overhead reflux drums, and phase separators in order to be effective. These systems are particularly costly to procure and erect. Extractive distillation towers for alkyl carbonate separation also require that an appropriate temperature profile be maintained across the column in order to obtain the desired distillation product cutpoints. These distillation temperature profiles generally conflict with maintaining optimum extraction process temperatures, resulting in cost penalties.

U.S. Pat. No. 4,428,753 to Bezman discloses a process for separating a binary mixture of water and isopropanol. The process requires mixing the aqueous isopropanol feedstock with gasoline blending hydrocarbons and coalescing the mixture in a mechanical separation coalescer. Such aqueous isopropanol separation processes are particularly difficult to operate since the gasoline blending hydrocarbon/isopropanol mixture is prone to emulsion formation. Breaking the emulsion and effectively separating the gasoline blending hydrocarbon/isopropanol and water mixture cannot generally be achieved without exotic and costly separation devices such as separating membranes, electrical devices, and/or beds of granular particulate.

Methods for concentrating solutions containing an alcohol and oxygenates such as organic ethers, aldehydes, ketones, and esters using physical separation means are also known in the art.

U.S. Pat. No. 4,798,674 to Pasternak et al. discloses a process for concentrating mixtures containing dimethyl carbonate and methanol using a membrane-based pervaporation step.

"Opportunities For Membranes in the Production of Octane Enhancers," by Shah et al., AICHE Spring 1989 National Meeting, Symposium Series, Vol. 85, No. 272, pgs. 93-97, also discloses a process for separating dimethyl carbonate and methanol azeotropes across a membrane using pervaporation.

However, physical membrane separation systems such as those described have not been effectively used in binary systems wherein water and alkyl carbonate or water and alkanol have been the constituents. Moreover, membrane systems have not been particularly reliable in industrial environments and have been known to present operability problems.

It has now been found that feedstocks comprising alkyl carbonate and water can be separated using liquid-liquid extraction, into an extract stream comprising a substantial amount of the alkyl carbonate present in the feedstock and a raffinate stream comprising a substantial amount of the water present in the feedstock. The liquid-liquid process is conducted with a hydrocarbon extraction solvent selective for alkyl carbonate relative to water.

It has also been found that a hydrocarbon extraction solvent selective for extracting alkyl carbonate over alkanol having a specific gravity of greater than 0.60 and less than 1.0 provides enhanced liquid-liquid extraction performance through improved raffinate/extract disengaging.

It has also been found that a solvent selective for extracting alkyl carbonates having an aromatic hydrocarbon concentration by weight of greater than 1 percent and an olefinic hydrocarbon concentration by weight of below 80 percent, provides improved extraction of alkyl carbonate from a feedstock comprising alkyl carbonate and water.

It has also been found that several hydrocarbon streams generally available in conventional petroleum refineries are suitable hydrocarbon extraction solvents including, but not limited to catalytic reformate, catalytic cracking process naphtha, heavy virgin naphtha, isomerate, alkylate, and the aromatic derivatives of various refinery streams including benzene, toluene, xylene, and combinations thereof.

It is therefore an object of the present invention to provide an extraction process for a feedstock comprising alkyl carbonate and water that recovers a substantial portion of the alkyl carbonate to an extract product stream and a substantial portion of the water product to a raffinate product stream.

It is another object of the present invention to provide a process that does not require costly extractive distillation columns for alkyl carbonate separation or require distillation column temperature profiles that are inconsistent with optimum extraction temperatures.

It is yet another object of the present invention to provide a process that does not require physical separation means, such as membrane systems, which can be unreliable in an industrial environment.

It is still another object of the present invention to provide a process that does not require the use of large volumes of costly aprotic polar solvents, utilizes several hydrocarbon streams generally present in a petroleum refinery, and does not require complete recovery of the hydrocarbon extraction solvent where the alkyl carbonate is to be blended for fuels use.

Other objects appear herein.

SUMMARY OF THE INVENTION

The above objects can be achieved by providing a process for separating alkyl carbonate from a feedstock comprising at least one alkyl carbonate and at least 0.01 percent by weight water comprising extracting the alkyl carbonate from the feedstock in a liquid-liquid extraction step comprising an extraction solvent selective for extracting alkyl carbonates relative to water in an amount sufficient to extract a substantial amount of the alkyl carbonates from the feedstock. The extraction solvent substantially comprises hydrocarbon boiling at a temperature ranging from about 50° F. to about 700° F. at atmospheric pressure and having a specific gravity ranging from about 0.50 to about 1.00.

In another embodiment, the above objects can be achieved by providing a process for separating alkyl carbonate from a feedstock comprising at least one alkyl carbonate, at least one alkanol, and at least 0.10 percent by weight water comprising fractioning the feedstock by distillation into an overhead product comprising a substantial fraction of alkanol and alkyl carbonate and a bottoms product comprising alkyl carbonate and water. The alkyl carbonate is extracted from the bottoms product comprising alkyl carbonate and water in a liquid-liquid extraction step comprising an extraction solvent selective for extracting alkyl carbonate relative to water in an amount sufficient to extract a substantial amount of the alkyl carbonate from the feedstock. The extraction solvent substantially comprises hydrocarbon boiling at a temperature ranging from about 50° F. to about 700° F. at atmospheric pressure and has a specific gravity ranging from about 0.60 to about 1.00.

In still another embodiment, the above objects can be achieved by providing a process for separating alkyl carbonate from a feedstock comprising at least one alkyl carbonate, at least one alkanol, and at least 0.10 percent by weight water comprising fractionating the feedstock by distillation extraction into an overhead product comprising alkyl carbonate and water and a bottoms product comprising a substantial fraction of alkanol and water utilizing an extractive distillation solvent selective for extracting alkanol relative to alkyl carbonate comprising water in an amount sufficient to separate a substantial fraction of the alkanol from the feedstock. The alkyl carbonate is extracted from the overhead product comprising alkyl carbonate and water in a liquid-liquid extraction step comprising an extraction solvent selective for extracting alkyl carbonate relative to water in an amount sufficient to extract a substantial amount of the alkyl carbonate from the feedstock. The extraction solvent substantially comprises hydrocarbon boiling at a temperature ranging from about 50° F. to about 700° F. at atmospheric pressure and has a specific gravity ranging from about 0.60 to about 1.00.

The process of the present invention provides substantial benefits over any of the processes or combinations of processes taught in the art.

The process of the present invention can provide substantial separation of alkyl carbonates from water in a single unitary liquid-liquid extraction column. The process of the present invention can also provide substantial separation of mixtures of alkyl carbonates having various and different alkyl radicals from water. Moreover, the process operates at alkyl carbonate extraction column temperature profiles that are entirely independent of distillation steps, which permits further optimization of the liquid-liquid extraction step. Similarly, the subject liquid-liquid extraction step does not require reboilers, condensers, and other costly and energy intensive equipment that are generally provided along with distillation towers.

The process of the present invention utilizes a readily available hydrocarbon stream as the solvent selective for extracting alkyl carbonate relative to water. The process does not require costly pure polar aprotic solvents which further mandate costly solvent recovery steps. However, the refiner retains the flexibility to add solvent recovery steps downstream of the extraction step to reduce solvent requirements. Since many conventional refinery hydrocarbon streams can be used as the solvent selective for extracting alkyl carbonate, the refiner can choose not to recover the solvent and operate on a once-through basis.

The process of the present invention operates at substantially lower solvent to feed ratios than processes in the art. For purposes of the present invention, the term solvent to feed ratio shall mean the total volume of hydrocarbon extraction solvent added per volume of alkyl carbonate present in the feedstock to the liquid-liquid extraction column. Lower solvent to feed ratios translate into reduced processing costs and permit the erection of smaller extraction devices.

BRIEF DESCRIPTION OF THE INVENTION

Suitable feedstocks for use with the extraction separation step of the present invention generally comprise alkyl carbonate and water. The feedstock generally comprises from about 50.0 percent by weight to about 99.99 percent by weight alkyl carbonate, preferably from about 80.0 percent by weight to about 99.99 percent by weight alkyl carbonate, and more preferably from about 90.0 percent by weight to about 99.99 percent by weight alkyl carbonate for best results. The water component is generally present in the extraction step feedstock in an amount ranging from about 0.01 percent by weight to about 50.0 percent by weight, commonly from about 0.10 percent by weight to about 20.0 percent by weight, and often from about 0.50 percent by weight to about 10.0 percent by weight.

It is also anticipated that the extraction step feedstock for use with the present invention may be derived from alkyl carbonate production process intermediate streams comprising alkyl carbonate, water, and unconverted alkanol. Where the extraction step feedstock is derived from an alkyl carbonate production process intermediate stream feedstock comprising unconverted alkanol, the intermediate stream feedstock generally comprises from about 5.0 percent by weight to about 99.0 percent by weight alkyl carbonate, preferably from about 10.0 percent by weight to about 90.0 percent by weight alkyl carbonate, and more preferably from about 10.0 percent by weight to about 50.0 percent by weight alkyl carbonate for best results. The alkanol component is generally present in the intermediate steam feedstock in an amount ranging from about 1.0 percent by weight to about 99.0 percent by weight, commonly from about 10.0 percent by weight to about 95.0 percent by weight, and often from about 50.0 percent by weight to about 90.0 percent by weight. Water is generally present in the feedstock in an amount ranging from about 0.1 percent by weight to about 20.0 percent by weight, commonly from about 1.0 percent by weight to about 15.0 percent by weight, and often from about 2.0 percent by weight to about 10.0 percent by weight.

Suitable alkyl carbonate components generally have an alkyl radical with from 1 to 20 carbon atoms. The preferred alkyl carbonates are the dialkyl carbonates and in particular, dimethyl carbonate and diethyl carbonate. The alkyl carbonate can also include dialkyl carbonates comprising two different alkyl radicals. Wherein the dialkyl carbonate comprises two different alkyl radicals, the preferred dialkyl carbonate is methyl ethyl carbonate. Similarly, the alkyl carbonate component can comprise a combination of alkyl carbonates having various and different alkyl radicals.

While any of the above-described alkyl carbonates are suitable for use with the process of the present invention, it is recognized that an end use for the separated alkyl carbonates can be as a gasoline blending component. Where gasoline is the end product to which the alkyl carbonate is blended, it is preferred that the alkyl radical contain less than 9 carbon atoms, preferably less than 5 carbon atoms, and more preferably less than 4 carbon atoms for best results. It is also preferable that the alkyl carbonate substantially boil within the temperature range of from about 50° F. to about 450° F. at atmospheric pressure. Alkyl carbonate alkyl radicals having more than 8 carbon atoms are not generally blended to gasoline since their end point temperature can exceed the end point temperature specification of many gasolines. Where petroleum distillates such as furnace oil and diesel fuel are the end products to which the alkyl carbonate is blended, it is preferable that the alkyl carbonate alkyl radical have from 6 to 20 carbon atoms and that a substantial portion of the alkyl carbonate boil within a temperature span ranging from about 250° F. to about 700° F. at atmospheric pressure for best results.

Another factor to be taken into consideration with regard to alkyl carbonate selection for gasoline use is that while dimethyl carbonate and diethyl carbonate have similar blending octanes in terms of the average of research plus motor octane, diethyl carbonate advantageously has a lower RVP (3 psia as compared to 10 psia). This advantage is particularly beneficial to petroleum refiners in view of a recent Environmental protection Agency decision to reduce the RVP requirements for gasolines well below the 10 psia blending RVP of dimethyl carbonate.

The cost of ethanol relative to methanol may also be factored into a decision of which alkyl carbonate feedstock component to process in accordance with the process of the present invention. External factors such as ethanol subsidies generally can and often do affect the economic balance between methanol and ethanol.

Additionally, the demand for methanol and ethanol for ether manufacture may also effect the raw material costs of alkanol feedstocks for the production of alkyl carbonates.

Unconverted alkanol components that can be present in the intermediate stream feedstock and to a lesser degree, the liquid-liquid extraction step feedstock, generally include alkanols having from 1 to 9 carbon atoms, commonly from 1 to 4 carbon atoms, and often from 1 to 3 carbon atoms. Generally, the alkanol in the feedstocks will correspond to the alkyl radical of the alkyl carbonate. For example, where dimethyl carbonate is the alkyl carbonate, methanol is generally one of the alkanols present in the feedstock. Correspondingly, where diethyl carbonate is the alkyl carbonate, ethanol is generally one of the alkanols present in the feedstock.

Mixtures of alkanols can also be present in the intermediate stream or liquid-liquid extraction step feedstocks of the process of the present invention Alkanols can also be injected into the intermediate stream or liquid-liquid extraction step feedstocks from external sources. For example, the feedstocks can be supplemented with various refinery streams that contain hydrocarbon which can be managed in a manner similar to that described in the present invention. It is anticipated that various refinery and chemical plant streams may contain components that can be separated and recovered utilizing the downstream separation steps described herein. For example, refinery ether production facilities can be integrated with the process of the present invention to consolidate alkanol separation and recovery equipment into a single cost-effective system. In this manner, alkanols can enter the process from external and supplemental injections. Where the alkanol stream is recovered from the process of the present invention and recycled back to the carbonate formation step, the alkanol from the external and supplemental stream can also reappear in the intermediate stream or, to a lesser extent, in the liquid-liquid extraction step feedstocks comprising the alkyl carbonate.

The water component of the intermediate stream or extraction step feedstocks of the present invention is generally formed as a by-product of many conventional alkyl carbonate-forming reactions. Where water is particularly undesirable with prior art processes due to the formation of azeotropes which can complicate separation steps, water does not pose a substantial operating limitation with the process of the present invention. In fact, the process of the present invention is specifically designed to accommodate relatively high water concentrations in the various feedstocks.

Sources for the alkyl carbonate component of the feedstock processed in accordance with the present invention can and generally include carbonate manufacturing processes, including but not limited to the carbonylation of alcohols, alkylene carbonate alcoholysis, urea alcoholysis, inorganic methods such as alkylation of metal carbonates, phosgene alcoholysis, among other hypothetical methods that may not have been proven effective or performed commercially.

The source of the alkyl carbonate component and the alkanol can be particularly important in optimizing implementation of the process of the present invention. For example, there can be several source locations in an alkyl carbonate manufacturing process that may provide suitable feedstock streams for use in accordance with the present invention. The feedstock may also be a combination of streams from various locations along the carbonate manufacturing facility. It is anticipated that optimization of the process may dictate that a fraction of one or more of several streams from several locations in various carbonate and alkanol source processes may feed the subject inventive process. These streams may be processed directly to the liquid-liquid extraction step or accommodated along with other intermediate streams in a preprocessing step prior to the liquid-liquid extraction step. Similarly, any recovered products such as alkanol or alkyl carbonate can be processed and recycled, in whole or in part, to various locations on the source facility in order to maximize economic gain. All of the fundamental integrations and optimizations described hereabove are envisioned as embodiments of the process of the present invention.

Figure 1:
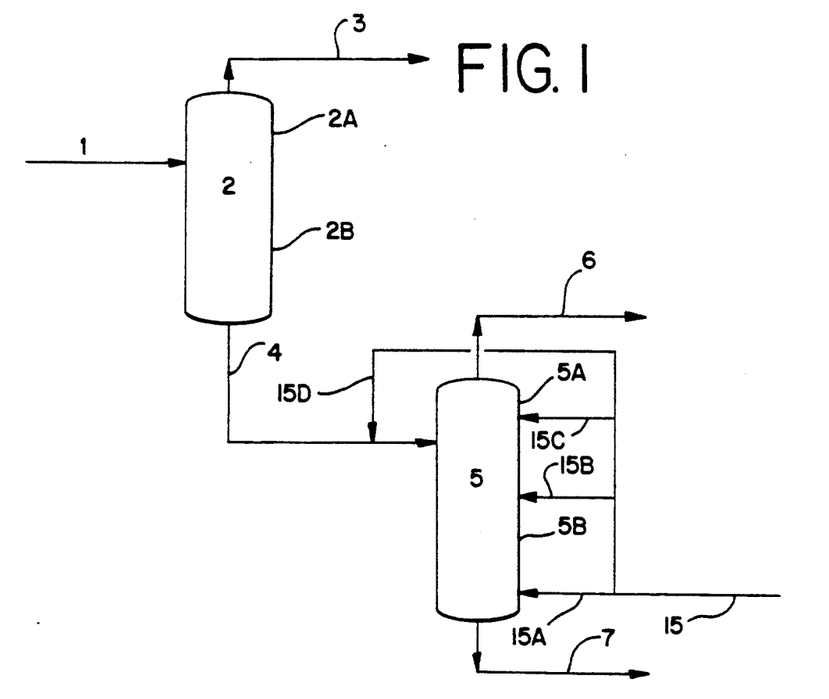
FIG. 1 is a process flow diagram of an alkyl carbonate extraction process in accordance with the process of the present invention including an alkyl carbonate, water, and alkanol distillation step upstream of the liquid-liquid extraction step.

FIG. 1 is a process flow diagram of an alkyl carbonate extraction process in accordance with the process of the present invention including an alkyl carbonate, water, and alkanol distillation step upstream of the liquid-liquid extraction step.

Figure 2:
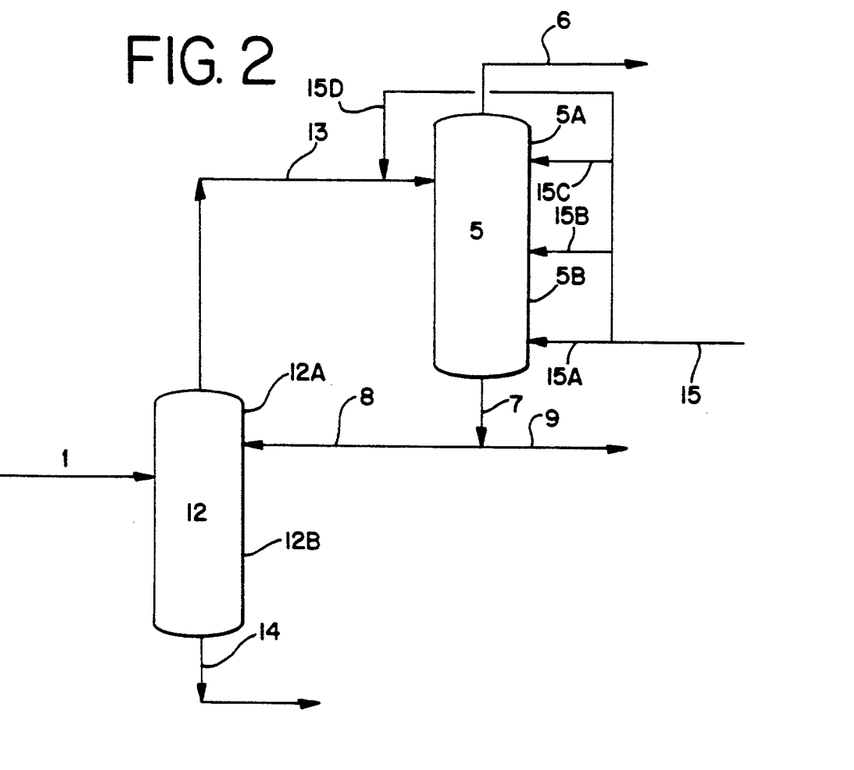
FIG. 2 is a process flow diagram of an alkyl carbonate extraction process in accordance with the process of the present invention including an alkyl carbonate, water, and alkanol extraction distillation step upstream of the liquid-liquid extraction step.

FIG. 2 is a process flow diagram of an alkyl carbonate extraction process in accordance with the process of the present invention including an alkyl carbonate, water, and alkanol extraction distillation step upstream of the liquid-liquid extraction step.

The preferred upstream preprocessing steps of the processes described in FIGS. 1 and 2 will be described independently, while the description of the downstream phases will be consolidated. To the extent the equipment and streams are equivalent for both FIGS. 1 and 2, they are numbered identically. It is fully anticipated that the process of the present invention can operate effectively without any or all of the preferred upstream preprocessing steps.

The preferred upstream processing steps are generally most useful with alkyl carbonate/alkanol/water mixtures where the vapor-liquid equilibrium and liquid-liquid equilibrium characteristics of such mixtures combine to make the upstream processing steps a viable and useful source of alkyl carbonate and water. The downstream step is generally useful for any and all alkyl carbonate and water mixtures, including most alkyl carbonates, symmetrical or asymmetrical or mixtures thereof.

In FIG. 1, the intermediate stream feedstock, comprising alkyl carbonate, alkanol, and water is conveyed through conduit 1 to a distillation column or tower 2. The distillation column 2 generally comprises a top rectification or rectifying section 2A which is the section of the distillation column located above the feedstock inlet and a bottom stripper or stripping section 2B located below the feedstock inlet and below the rectifying section 2A.

The feedstock from conduit 1 is fractionated by distillation into an overhead product exiting the column through conduit 3 and a bottoms product exiting the column through conduit 4. The overhead product from conduit 3 generally comprises a substantial fraction of the alkanol component entering the column through conduit 1. For purposes of the present invention, the term a "substantial fraction" of the alkanol component entering the column through conduit 1 shall mean at least 80 percent of the alkanol calculated as a ratio by weight. The balance of the overhead stream exiting through conduit 3 generally comprises alkyl carbonate with minor amounts of water. The distillation column 2 is preferably designed and operated in a manner such that less than 50.0 percent of the alkyl carbonate entering the column, calculated as a ratio by weight and preferably less than 20.0 percent of the alkyl carbonate entering the column, exits the column as overhead product. The overhead product is generally redirected back to the alkyl carbonate production process or conveyed to an alkanol/alkyl carbonate separation process specically associated with the alkyl carbonate recovery process or connected with another process operating similar facilities.

The bottoms product from conduit 4 generally comprises a substantial fraction of the alkyl carbonate component (defined hereabove) entering the column through conduit 1. The balance of the bottoms stream exiting through conduit 4 generally comprises water with minor amounts of alkanol. The distillation column 2 is preferably designed and operated in a manner such that less than 20.0 percent of the alkanol entering the column, calculated as a ratio by weight and preferably less than 5.0 percent of the alkanol entering the column, exits the column as bottoms product. The bottoms product from conduit 4 provides the extraction step feedstock for alkyl carbonate/water extraction separation in accordance with the present invention.

In FIG. 2, the intermediate stream feedstock, comprising alkyl carbonate, alkanol, and water is conveyed through conduit 1 to a distillation extraction column or tower 12. The distillation extraction column 12 generally comprises a top rectification or rectifying section 12A which is the section of the distillation extraction column located above the feedstock inlet and a bottom stripper or stripping section 12B located below the feedstock inlet and below the rectifying section 12A. The solvent stream selective for extracting alkanol relative to alkyl carbonate and generally comprising water is conveyed to the distillation extraction column 12 through conduit 8 and is commonly conveyed into the distillation extraction column rectification section 12A.

The feedstock from conduit 1 is fractionated by distillation extraction into an overhead product exiting the column through conduit 13 and a bottoms product exiting the column through conduit 14. The distillation extraction column reverses the overhead product and bottoms product orientation compared to the process illustrated in FIG. 1. In the subject distillation extraction column, the bottoms product from conduit 14 generally comprises a substantial fraction of the alkanol component (defined hereabove) entering the column through conduit 1 with the balance of the stream comprising water and minor amounts of alkyl carbonate. The distillation extraction column 12 is preferably designed and operated in a manner such that less than 10.0 percent of the alkyl carbonate entering the column, calculated as a ratio by weight and preferably less than 5.0 percent of the alkyl carbonate entering the column, exits the column as bottoms product. The bottoms product is generally redirected back to the alkyl carbonate production process or conveyed to an alkanol/water separation process specifically associated with the alkyl carbonate recovery process or connected with another process operating similar facilities.

The overhead product from conduit 13 generally comprises a substantial fraction of the alkyl carbonate component (defined hereabove) entering the column through conduit 1. The balance of the overhead stream exiting through conduit 13 generally comprises water with minor amounts of alkanol. The distillation column 12 is preferably designed and operated in a manner such that less than 10.0 percent of the alkanol entering the column, calculated as a ratio by weight and preferably less than 5.0 percent of the alkanol entering the column, exits the column as overhead product. The overhead product from conduit 13 provides the extraction step feedstock for alkyl carbonate/water extraction separation in accordance with the present invention.

The overhead product from conduit 13 can also be cooled across a heat exchanging device such as an air or water cooled heat exchanger to create a two-phase (liquid-liquid) product comprising an alkyl carbonate-rich bottom phase and a water-rich top phase. The water-rich top phase can be decanted and recycled to conduit 8. The alkyl carbonate-rich bottom phase provides an improved feed for downstream liquid-liquid extraction.

Streams 4 and 13 in FIGS. 1 and 2 respectively are directed to liquid-liquid extraction column or tower 5. The liquid-liquid extraction column 5 generally comprises a top rectification or rectifying section 5A which is the section of the extraction column located above the feedstock inlet and a bottom stripper or stripping section 5B located below the feedstock inlet and below the rectifying section 5A. The hydrocarbon extraction solvent stream is conveyed to the distillation extraction column through conduits 15A, 15B, 15C, and 15D from source conduit 15 and can be conveyed into the liquid-liquid extraction column rectification section 12A, stripping section 12B, and/or with the feedstock from conduits 4 and 13. The rectification section 5A of the liquid-liquid extraction column 5 is optional and can reduce the amount of water that escapes overhead as a result of turbulence and water entrainment that can occur at the separation tray or mechanism correlating to the feedstock inlet location.

The solvent extraction column generally provides a particular number of theoretical stages of solvent extraction separation. For purposes of the present invention, the term theoretical stage of separation shall be defined as a separation step wherein the solvent extracted extract stream and raffinate stream from the extraction step exist in perfect equilibrium with each other at a particular set of process conditions and stage compositions and wherein the facilities exist for separating the product streams. The number of theoretical stages of separation may be provided by a substantially larger number of mechanical plates or trays than the projected number of theoretical stages, wherein plate or tray efficiencies are below 100 percent.

The extraction solvent, comprising hydrocarbon selective for extracting alkyl carbonates relative to water and alkanol is added to the liquid-liquid extraction column 5 through one or more of conduits 15A, 15B, 15C, and 15D. It is anticipated that other cosolvents may be added to the extraction column to remove impurities or to improve alkyl carbonate extraction but such solvents are not generally necessary to practice the present invention. The extraction solvent generally proceeds upwardly through the column and countercurrently with and to portions of feedstreams 4 and 13 comprising substantially alkyl carbonate and water to preferentially extract alkyl carbonate from the liquid-liquid extraction column feedstock.

An overhead stream or extract is withdrawn from the top of the extraction column through conduit 6. The extract stream generally contains a substantial amount of the alkyl carbonate component from the feedstock and the extraction solvent selective for extracting alkyl carbonates. The extract stream from conduit 6 can be directed to a separation vessel for solvent recovery and recycling to the extraction column or to storage wherein the process is once-through solvent extraction. Separation vessels can be provided for separating the extract stream into a stream containing a high concentration of the alkyl carbonate component and a stream containing a high concentration of the extraction solvent. Suitable separation vessels can be, but are not limited to single stage flash separators, distillation columns, stripper columns, among other separation devices known to those skilled in the art of chemical separation. The stream containing a high concentration of alkyl carbonate can fulfill any of numerous end uses including, but not limited to use as a commercial chemical or as a gasoline or distillate blending component. The stream containing a high concentration of the extraction solvent is commonly conveyed back to the process such as through solvent supply conduit 15.

A bottoms stream or raffinate stream is withdrawn from the bottom of the liquid-liquid extraction column 5 through conduit 7. The raffinate stream generally contains a substantial portion of the water component from the feedstock and can comprise minor amounts of alkyl carbonate and other impurities that can be present in the extraction column feed. The raffinate stream from conduit 7 can be directed for further processing such as through conduit 7 in FIG. 1 or conduit 9 in FIG. 2, recycled back to the distillation extraction column 12 in FIG. 2 through conduit 8, recycled back to the alkyl carbonate manufacturing process, or can be directed to other alkyl carbonate, alkanol, and/or water reclamation processes present at the facility or elsewhere. It is generally important to effectively recover and recycle streams comprising water such as the extraction column 5 bottoms product 7 in order to minimize water recovery and reclamation costs.

The solvent suitable for injection into distillation extraction columns such as that shown as distillation extraction column 12 in FIG. 2, generally comprises a solvent selective for extracting alkanol relative to alkyl carbonate. The preferred distillation extraction solvent is water provided in an amount sufficient to extract a substantial portion of the alkanol from the feedstock.

While water is the preferred distillation extraction solvent, it is important to note that waste water minimization is an important objective of modern petroleum refineries. Since it is anticipated that there may and generally will be some fraction of water present in the feedstock, the water that is used as the distillation extraction solvent can be recovered from the feedstock and reused for extraction. It is preferred that the process in accordance with the present invention, under steady state operation, not import or minimize the import of water into the process.

Where water is imported into the process, the stream comprising water can be derived from other processes in order to minimize total refinery waste water. These water-containing streams may also contain hydrocarbon and other components in addition to water. It is recommended that the distillation extraction solvent comprising water be analyzed to check for impurities that can adversely effect the extraction process or contaminate downstream products.

The distillation extraction solvent is generally added to the distillation extraction column at a solvent to feed volume ratio based on the total volume of solvent added (from all locations) per volume of alkanol present in the feedstock. The solvent to feed ratio is generally adjusted to provide the desired alkanol extraction performance level desired. The distillation extraction solvent to feed ratio for the process of the present invention generally ranges from about 1:0.02 to about 1:2, preferably from about 1:0.05 to about 1:1, and more preferably from about 1:0.08 to about 1:0.5.

The distillation extraction solvent can generally be loaded in a manner so as to produce a distillation extraction bottoms stream containing from about 1 percent by weight to about 70 percent by weight of alkanol in the total bottoms stream, commonly from about 3 percent by weight to about 50 percent by weight, and often from about 9 percent by weight to about 30 percent by weight. The distillation extraction solvent loading is also a function of the number of theoretical stages of separation in the distillation extraction column and columns with more theoretical stages can generally achieve greater loadings. Exceeding the loading ranges described above, however, can result in alkanol losses to the overhead stream or alkyl carbonate losses to the bottoms stream. Similarly, the process of the present invention can achieve low alkanol loss levels to the overhead stream of less than 10 percent by weight of the overhead stream, commonly less than 2 percent by weight of the overhead stream, and often less than 1 percent by weight of the overhead stream.

Overall, the distillation extraction step in accordance with the present invention generally recovers a substantial amount of the alkanol to the distillation extraction bottoms stream. For purposes of the present invention, a "substantial amount of alkanol recovery" shall mean the recovery of at least 50 percent of the alkanol present in the feedstock directed to the distillation extraction column to the bottoms stream, calculated as a ratio by weight. It is not uncommon however, for alkanol recoveries to exceed as much as 80 percent and often as much as 90 percent or higher.

The distillation step for preprocessing intermediate streams to provide a feedstock suitable for liquid-liquid extraction in accordance with the present invention is generally conducted at average temperatures ranging from about 140° F. to about 392° F., preferably from about 140° F. to about 302° F., and more preferably from about 140° F. to about 212° F. for best results. Operating pressures generally range from about 0 psig to about 400 psig and preferably from about 0 psig to about 150 psig for best results.

The distillation extraction step for preprocessing intermediate streams to provide a feedstock suitable for liquid-liquid extraction in accordance with the present invention is generally conducted at average temperatures ranging from about 158° F. to about 392° F., preferably from about 167° F. to about 302° F., and more preferably from about 176° F. to about 230° F. for best results. Operating pressures generally range from about 0 psig to about 400 psig and preferably from about 0 psig to about 50 psig for best results.

The hydrocarbon extraction solvent for use with the liquid-liquid extraction step generally comprises a hydrocarbon solvent selective for extracting alkyl carbonate relative to water and having a low water miscibility. Hydrocarbon extraction solvents having low polarity generally provide improved selectivity for extracting alkyl carbonate relative to water. Suitable hydrocarbon solvents selective for extracting alkyl carbonate relative to water generally have a specific gravity ranging from about 0.50 to about 1.00, preferably from about 0.60 to about 0.95, and more preferably from about 0.60 to about 0.90 for best results. Hydrocarbon having a specific gravity within these ranges generally facilitates better mixing and extraction performance wherein suitable recoveries of alkyl carbonate to extract and water to raffinate can be achieved with fewer theoretical stages of separation. Moreover, the entrainment of hydrocarbon extraction solvent and water in the extract phase, often indicated by a hazy appearing extract product, is substantially reduced wherein the solvent is within the above specific gravity ranges.

Preferably, the hydrocarbon extraction solvent has an aromatics concentration of more than 1.0 percent by weight and preferably ranging from about 5.0 percent by weight to about 50.0 percent by weight and more preferably from about 10.0 percent by weight to about 40.0 percent by weight for best results. It has been found that the aromatics concentration of the hydrocarbon extraction solvent correlates favorably with the effectiveness of the solvent for extracting alkyl carbonates. However, where aromaticity becomes excessive, the specific gravity can increase beyond a level where extract/raffinate separability adversely affects solvent extraction performance.

Preferably, the extraction solvent has an olefin concentration of less than 80.0 percent by weight and preferably ranging from about 0.0 percent by weight to about 40.0 percent by weight and more preferably from about 0.0 percent by weight to about 25.0 percent by weight for best results. It has also been found that very high olefin concentrations (greater than 80.0 percent by weight) in the hydrocarbon extraction solvent correlates inversely with the effectiveness of the solvent for extracting alkyl carbonates.

It has also been found that high proportions of branched paraffinic components can also adversely affect solvent extraction performance. Such components are most commonly present in refinery alkylation and isomerate unit products.

Gasoline boiling range components found in conventional petroleum refineries and chemical plants satisfy many of the hydrocarbon extraction solvent criteria described above. Suitable extraction solvents generally comprise most refinery hydrocarbon streams boiling at a temperature ranging from about 50° F. to about 450° F. at atmospheric pressure. These streams include, but are not limited to fluid catalytic cracking process naphtha, fluid or delayed coking process naphtha, light virgin naphtha, heavy virgin naphtha, hydrocracker naphtha, hydrotreating process naphthas, alkylate, isomerate, catalytic reformate, and the aromatic derivatives of these streams such as benzene, toluene, xylene, and combinations thereof. The catalytic reformate and catalytic cracking process naphthas can often be split into narrower boiling range streams such as light and heavy catalytic naphtha and light and heavy reformate which can be specifically customized for use as a solvent in accordance with the present invention. The preferred streams are light virgin naphtha, catalytic cracking naphthas including light catalytic cracking unit naphtha, catalytic reformate including light reformate, and the aromatic derivatives of refinery hydrocarbon streams including benzene and toluene. The most preferred streams are light reformate and light catalytic cracking unit naphtha.

Distillate boiling range hydrocarbon has not been regulated for oxygenate content at this time. Therefore, the need for an inexpensive oxygenate for distillate fuels such as diesel fuel and furnace oil is not as pressing as for gasoline. However, distillates also satisfy many of the hydrocarbon extraction solvent criteria described above and can be effective extraction solvents. Suitable distillate-containing extraction solvents generally comprise refinery hydrocarbon streams boiling at a temperature ranging from about 150° F. to about 700° F. at atmospheric pressure and preferably from about 250° F. to about 700° F. at atomospheric pressure for best results. These streams include, but are not limited to virgin light middle distillate, virgin heavy middle distillate, fluid catalytic cracking process light catalytic cycle oil, coker still distillate, hydrocracker distillate, hydrotreating process distillate, and the hydrotreated embodiments of these streams. The preferred streams are the hydrotreated embodiments of fluid catalytic cracking process light catalytic cycle oil, coker still distillate, and hydrocracker distillate.

It is also anticipated that one or more of the above hydrocarbon streams can be combined for use as a hydrocarbon extraction solvent. In many cases, extraction performance for the various solvent alternatives may be similar. In these cases, logistics such as the volume availability of a stream, location of the nearest connection, and short term economics may be determinative as to what solvent is utilized. Therefore, the process of the present invention offers substantial flexibility as to solvent alternatives. A further advantage of the nonpolar hydrocarbon extraction solvent of the present invention is that the solvent need not be recovered from the overhead extract stream and can proceed directly to gasoline or distillate blending along with the recovered alkyl carbonate. It is preferred that gasoline and distillate solvents not be commingled as this may require one or more additional separation steps.

The hydrocarbon extraction solvent is generally added to the liquid-liquid extraction column at a solvent to feed volume ratio based on the total volume of solvent added (from all locations) per volume of alkyl carbonate present in the feedstock. The extraction solvent to feed ratio is generally adjusted to provide the desired alkyl carbonate extraction performance level desired. The hydrocarbon extraction solvent to feed ratio for the process of the present invention generally ranges from about 30:1 to about 1:1 and commonly from about 10:1 to about 3:1. The extraction solvent and alkyl carbonate extraction process in accordance with the present invention provides superior selectivity and substantially lower solvent to feed ratios compared to many of the polar aprotic solvents generally described in the art.

The extraction solvent can generally be loaded in a manner so as to produce an extract containing from about 1 percent by weight to about 50 percent by weight of alkyl carbonate in the total overhead extract stream, commonly from about 5 percent by weight to about 40 percent by weight, and often from about 10 percent by weight to about 30 percent by weight. The extraction solvent loading is, to some extent, a function of the number of theoretical stages of separation in the extraction column. Columns with more theoretical stages can achieve greater loadings and hence, can operate at lower solvent to feed ratios. Exceeding the loading ranges described above, however, can result in alkyl carbonate losses to the raffinate stream or water breakthrough to the extract stream. Similarly, the process of the present invention can achieve low alkyl carbonate loss levels to the raffinate stream of less than 15 percent by weight of the raffinate, commonly less than 2 percent by weight of the raffinate, and often less than 0.1 percent by weight of the raffinate. At the same time, the extraction solvent is highly selective wherein the extract leaving the extraction column generally comprises less than 10 percent by weight water, commonly less than 1 percent by weight water, and often less than 0.1 percent by weight water.

Where the process of the present invention is utilized with multiple alkyl carbonates, the process can be operated to continue to partition the various alkyl carbonates to the extract stream while partitioning water to the bottoms raffinate stream. This capability is quite useful and permits the operator to separate such multiple alkyl carbonates from water in a single operation. This aspect of the present invention provides substantial benefits to the refiner faced with the obstacle of recovering a mixture of alkyl carbonates with wide and diverse boiling point temperatures from an aqueous stream. It is important to note, however, that where multiple alkyl carbonates are processed in a single unitary extraction tower, additional theoretical stages of separation may be required beyond the number of theoretical stages expected for a single alkyl carbonate and the efficiency of separation could be lower.

Overall, the process in accordance with the present invention generally recovers a substantial amount of the alkyl carbonate to the extract stream. For purposes of the present invention, a "substantial amount of alkyl carbonate recovery" shall mean the recovery of at least 50 percent by weight of the alkyl carbonate present in the feedstock to the extract stream. It is not uncommon, however, for alkyl carbonate recoveries to exceed as much as 75 percent by weight and often as much as 90 percent by weight or higher.

It has also been found that the solvent extraction step for extracting alkyl carbonate from aqueous alkyl carbonate feedstocks can also be enhanced through other methods.

For example, it has been found that the process steps for extracting alkyl carbonate from an aqueous alkyl carbonate-containing feedstock can be enhanced further by adjusting the hydrocarbon extraction solvent injection points in the liquid-liquid extraction tower. Each theoretical stage of separation comprises a discrete composition of alkyl carbonate, water, and hydrocarbon extraction solvent among other components. Depending on these compositions, the solvent loading, and the process conditions attendant to these theoretical stages, it has been found that the process can be enhanced by aggressively identifying the best locations to add the hydrocarbon extraction solvent to favorably effect the extraction process. It has also been found that the preferable location for addition of a recycle solvent stream containing minor amounts of alkyl carbonate is at the stage in the liquid-liquid extraction column where the solvent composition most closely approximates the solvent composition at that stage without solvent recycle. Where the extraction solvent is fresh unprocessed hydrocarbon, it is generally preferable that at least a portion of the hydrocarbon extraction solvent be injected at the bottom of the liquid-liquid extraction column.

The liquid-liquid extraction step in accordance with the process of the present invention can be operated using numerous combinations of hardware and process variables, with various feedstock characteristics, and can be customized to meet wide-ranging product requirements. The overall extraction separation efficiency is generally a function of the number of theoretical stages of separation in the extraction column, whether the theoretical stages are rectifying or stripping, the choice and amount of hydrocarbon extraction solvent, the efficiency of the extraction device and internals, and the feedstock characteristics. For example, more theoretical stages in the rectification section can favorably reduce the level of water that is undesirably withdrawn with the extract, particularly where the rectifying and stripping sections are operated at different temperatures. Similarly, more theoretical stages in the stripping section and higher extraction solvent to alkyl carbonate ratios both favorably reduce the level of alkyl carbonate that is undesirably withdrawn with the raffinate. It has also been found that the particular alkyl radical with the alkyl carbonate can effect the solvent to feed requirements and/or theoretical stages required to extract the alkyl carbonate from the feedstock. For example, diethyl carbonate is generally more easily extracted from a feedstock than dimethyl carbonate and may require fewer theoretical stages or lower hydrocarbon extraction solvent to feed ratios.

The liquid-liquid extraction step in accordance with the present invention generally requires at least two theoretical stages of separation and more preferably at least three theoretical stages of separation for best results. It is also preferred that the process have at least one stage of rectifying extraction with at least 2 stages and more preferably at least 3 stages of stripping extraction for best results.

The various hardware alternatives for liquid-liquid extraction are generally known to those skilled in the art of chemical separation methods. Suitable liquid-liquid extraction methods include, but are not limited to, single and multiple solvent extraction and rotary extraction.

A commonly used liquid-liquid extraction device is the liquid-liquid extraction column. Liquid-liquid extraction can be conducted with a single solvent in a single mechanism, with dual solvents in a single mechanism, or as single extractions in series or in parallel. Liquid-liquid extraction is generally conducted counter-currently wherein the liquid having the higher specific gravity is added at a location high in the extraction column in a manner so that the liquid will proceed downwardly, and the liquid having the lower specific gravity is added at a location lower in the column in a manner so that the liquid will proceed upwardly. The higher or lower specific gravity liquids may be either the feedstock or the solvent in a single solvent extraction. Wherein dual solvents are employed, the counter-current principles and specific gravity considerations still generally apply.

The primary component extracted by the solvent along with the solvent exiting the extraction column is generally referred to as the extract stream. Where dual solvents are employed to extract multiple components and wherein one or more extract streams leave the top of the column and the one or more extract streams leave the bottom of the column, the extract stream is generally designated by the operator. For purposes of the present invention, the alkyl carbonate and hydrocarbon extraction solvent exiting the top of the liquid-liquid extraction column has been designated as the extract stream.

Liquid-liquid extraction columns can also define two distinct column operating sections known in the art as the rectification section or the rectifying section and the stripper section or stripping section. For purposes of the present invention, the rectification section will be defined as the volume of the liquid-liquid extraction column positioned above the primary feedstock inlet and the stripper section will be defined as the volume of the liquid-liquid extraction column positioned below the primary feedstock inlet.

Liquid-liquid extraction towers also generally comprise mixing and separation internals for increasing separation efficiency. These separation internals generally include mechanisms such as valve, sieve, or bubble cap trays or packing elements including, but not limited to, pall rings, grid packing, or other mechanisms known in the art. The higher the efficiency of these separation internals, the better the extraction performance.

Suitable liquid-liquid extraction devices can also include rotary extraction devices wherein the feedstock and solvent(s) are injected into a rotating cylinder comprising a plurality of holes within a cylinder shell. The cylinder is rotated at an angular velocity sufficient for the high specific gravity component to migrate outside of the cylinder and into the shell wherein it is removed, and the lower specific gravity component to migrate towards the center of the cylinder from where it is withdrawn.

Other separation methods and embodiments are also anticipated for use with the present invention from an understanding of chemical separation methods known in the art.

The liquid-liquid extraction column process conditions can comprise a single extraction temperature ranging from about 32° F. to about 200° F., preferably from about 32° F. to about 120° F., and more preferably from about 32° F. to about 100° F. for best results. Extraction column temperatures below 32° F. can result in the crystallization of the water and alkyl carbonate. Temperatures above these ranges can result in boiling and/or hydrolysis of the alkyl carbonate.

It has been found, however, that the effectiveness of the extraction of alkyl carbonate from the extraction step feedstock utilizing the hydrocarbon extraction solvent, can be improved wherein the stripper section reaction temperature is reduced. Where the rectification and stripper temperatures can be controllably maintained at different temperatures, it is preferred that the temperature of the rectification section be maintained at a temperature ranging from about 32° F. to about 200° F., more preferably from about 40° F. to about 160° F., and more preferably from about 50° F. to about 120° F. for best results. It is preferred that the stripper section be maintained at a lower temperature ranging from about 32° F. to about 150° F., preferably from about 32° F. to about 100° F., and more preferably from about 32° F. to about 50° F. for best results.

The lower extraction temperatures can be achieved by refrigerating the hydrocarbon extraction solvent prior to injection into the extraction column stripping section, by providing a refrigerated column pumparound system extending from the stripping section, by designing an internal cooling system within the stripping section of the extraction column such as cooling coils, or by other methods known in the art.

The liquid-liquid extraction column pressure generally ranges from about 0 psig to about 100 psig, preferably from about 0 psig to about 75 psig, and more preferably from about 0 psig to about 50 psig for best results. Extraction column pressure has not been shown to substantially effect extraction performance but can impact the maximum allowable extraction temperature.

The extract stream comprising alkyl carbonate and hydrocarbon extraction solvent can be directed to a separation step for concentrating alkyl carbonate and recovering the extraction solvent for recycling back to the extraction step. An extract stream separation step may not be necessary wherein a suitable and readily available gasoline blending component is utilized as the extraction solvent. However, concentration of the alkyl carbonate-containing extract into a rich alkyl carbonate stream can advantageously provide a higher oxygen-content and more homogenous oxygenate-containing gasoline or distillate blending component which can provide product blending efficiency/flexibility benefits.

Such an extract stream separation step can be a single stage flash or a multistage fractionation. The overhead product from such a separation will generally contain from about 30 percent by weight to about 100 percent by weight and commonly from about 40 percent by weight to about 80 percent by weight of alkyl carbonate. The balance of the overhead product generally comprises the hydrocarbon extraction solvent and minor amounts of impurities such as alkanol (less than 5 percent by weight) and water (less than 0.1 percent by weight). Preferably, the overhead stream comprises less than 1 percent by weight alkanol and water combined, and more preferably less than 0.1 percent by weight for best results.

The extract separation step can also be conducted in an existing refinery separation or fractionation system. Full-boiling range gasoline and distillate streams are commonly split or fractionated in modern refineries for various purposes including, but not limited to feedstock preparation for downstream processing units or gasoline blending advantages. It is anticipated that streams such as full-boiling range catalytic cracking unit naphtha, full-boiling range reformate, and full-boiling range crude unit naphtha can be used as the first extraction solvent in order to take advantage of existing downstream fractionator or splitter facilities. For example, for full-boiling range fluid catalytic cracking unit naphtha, reformate, and crude unit naphtha, the extract separation step in accordance with the present invention can be performed in a fractionator that separates fluid catalytic cracking unit naphtha into light and heavy fractions, reformate into light and heavy fractions, or crude unit naphtha into light and heavy fractions respectively.

Similarly, the separation step can be performed in a multiple-product fractionation system such as a crude unit atmospheric tower, a fluid catalytic cracking unit main fractionator, or other multiple-product systems that may also be present in a refinery. Multiple-product systems provide additional flexibility in that any one or more of several hydrocarbon solvent streams may be proximately located and suitable for use with the extraction process.

The bottoms product from such an extract separation generally comprises the extraction solvent and minor amounts of alkyl carbonate, alkanol, and water. This fraction can be recycled back to the liquid-liquid extraction step to reduce the amounts of make-up extraction solvent that must be added to the extraction column to maintain performance. The recycle fraction can be directed to the extraction solvent inlet line or can be directed independently to the extraction column in a more optimal location based on the composition of the stream. For example, it is preferred that fresh make-up extraction solvent be added to the bottom of the extraction column and recycle extraction solvent be added at higher locations in the extraction column where the recycled extraction solvent contains more alkyl carbonate than the fresh extraction solvent.

The raffinate stream comprising water and impurities such as minor amounts of alkanol can also be directed to a separation step for removing impurities and concentrating the water for recycling back to the extraction step, distillation extraction step, or reclamation. Recovered impurities such as alkanol can be directed to any one or more of several locations including, but not limited to the carbonate manufacturing process, an etherification process (i.e., MTBE, TAME, ETBE, etc.), directly or indirectly to gasoline blending, or to other processes requiring a stream with high alkanol content. The concentrated water stream from the separation step is generally recycled back to the distillation extraction step in a manner so as to reduce the net amount of water that must be environmentally reprocessed.

The process of the present invention provides substantial benefits over the processes or combinations of processes taught in the art.

The process of the present invention provides for substantial separation of alkyl carbonates from water and and other impurities or unconverted feedstocks such as alkanol in a single unitary liquid-liquid extraction column. The process of the present invention generally results in an extract product leaving a single unitary liquid-liquid extraction column with a water concentration of less than 10 percent by weight of the extract and a raffinate product with an alkyl carbonate concentration of less than 15 percent by weight of the raffinate.

The process of the present invention operates at a liquid-liquid extraction column temperature profile that is entirely independent of distillation steps which permits further process optimization of the liquid-liquid extraction step. An independent extraction column permits the refiner to operate the stripper extraction section at lower temperatures than the rectification section to improve extraction performance.

The process of the present invention facilitates addition of liquid-liquid extraction solvent recovery steps downstream of the extraction step to reduce solvent requirements. Since it has been found that many conventional refinery hydrocarbon streams can be used as the extraction solvent for extracting alkyl carbonate, the refiner can choose not to recover the extraction solvent and operate on a once-through basis. The refiner can also choose to use solvents that permit and enhance the use of existing gasoline or multiple-product fractionation systems for performing downstream separation steps.

The process of the present invention utilizes an extraction column for alkyl carbonate separation and not a distillation column or combination extraction distillation column. Distillation columns generally require reboilers, condensers, and other equipment and are generally more costly to procure and erect. Distillation columns are also generally more energy intensive and costly to operate.

The process of the present invention utilizes a readily available hydrocarbon stream as the extraction solvent. The process does not require costly pure polar aprotic solvents which further mandate costly solvent recovery steps.

The process of the present invention operates at substantially lower solvent to feed ratios than processes in the art. Lower solvent to feed ratios reduce processing costs and permit the construction of smaller extraction facilities.

The present invention is described in further detail in connection with the following examples, it being understood that the same are for purposes of illustration and not limitation.

EXAMPLE 1

Single-stage extractions were conducted in accordance with the present invention using various conventional gasoline component streams found in a petroleum refinery as the alkyl carbonate extraction solvent. The case studies were performed at bench scale using separatory funnels.

The feedstocks utilized for the tests contained 18 grams of dimethyl carbonate, 4 grams of water, and 44 grams of the particular test solvent. The solvents tested were light and heavy virgin naphthas (LVN and HVN) which generally comprise hydrocarbon having from between 4 and 7 carbon atoms and from 6 and 12 carbon atoms respectively that have been derived from crude without the benefit of a reaction or conversion step, light and total catalytic naphthas (LCN and TCN) which generally comprise naphthas having from 4 to 7 carbon atoms and from 4 to 12 carbon atoms respectively that have been derived from a fluid catalytic cracking or coking process, heavy and light ultraformate or reformate (HUF and LUF) which generally comprise a large fraction of aromatics having from about 6 to 12 carbon atoms and that have been derived from a catalytic reforming process, alkylate which generally comprises branched paraffins having from 6 to 12 carbon atoms, and toluene. The results of the single-stage extractions are provided in Table 2.

TABLE 2

| | ALKYL CARBONATE EXTRACTION SOLVENTS | | | | | | | |
|---|---|---|---|---|---|---|---|---|
| Balances, wt % | LVN | HVN | LCN | TCN | LUF | HUF | ALKYLATE | TOLUENE |
| Feed | | | | | | | | |
| DMC | 27.30 | 27.30 | 27.30 | 27.30 | 27.30 | 27.30 | 27.30 | 27.30 |
| Water | 6.00 | 6.00 | 6.00 | 6.00 | 6.00 | 6.00 | 6.00 | 6.00 |
| Solvent | 66.70 | 66.70 | 66.70 | 66.70 | 66.70 | 66.70 | 66.70 | 66.70 |
| Total, wt % | 100.00 | 100.00 | 100.00 | 100.00 | 100.00 | 100.00 | 100.00 | 100.00 |
| Products | | | | | | | | |
| Extract | | | | | | | | |
| DMC | 36.89 | 30.61 | 35.43 | 33.70 | 35.27 | 31.09 | 34.87 | 31.00 |
| Water | 0.17 | 0.19 | 0.17 | 0.20 | 0.23 | 0.25 | 0.18 | 0.87 |
| Solvent | 62.94 | 69.20 | 64.40 | 66.10 | 64.50 | 68.66 | 64.94 | 68.13 |
| Total, wt % | 100.00 | 100.00 | 100.00 | 100.00 | 100.00 | 100.00 | 100.00 | 100.00 |
| Raffinate | | | | | | | | |
| DMC | 6.86 | 6.99 | 5.80 | 6.01 | 4.74 | 5.04 | 7.91 | 3.67 |

TABLE 2-continued

| Balances, wt % | ALKYL CARBONATE EXTRACTION SOLVENTS | | | | | | ALKYLATE | TOLUENE |
|---|---|---|---|---|---|---|---|---|
| | LVN | HVN | LCN | TCN | LUF | HUF | | |
| Water | 92.93 | 92.82 | 94.09 | 93.84 | 25.11 | 94.82 | 91.84 | 96.04 |
| Solvent | 0.21 | 0.19 | 0.11 | 0.15 | 0.15 | 0.14 | 0.25 | 0.29 |
| Total, wt % | 100.00 | 100.00 | 100.00 | 100.00 | 100.00 | 100.00 | 100.00 | 100.00 |
| DMC Dist. Coeff., wt % E/wt % R | 5.35 | 4.37 | 6.11 | 5.61 | 7.44 | 6.16 | 4.41 | 8.45 |
| Density, g/cc | | | | | | | | |
| Solvent | 0.659 | 0.741 | 0.646 | 0.738 | 0.756 | 0.836 | 0.687 | 0.887 |
| Extract | 0.759 | 0.806 | 0.724 | 0.800 | 0.819 | 0.886 | 0.754 | 0.910 |
| Raffinate | 1.032 | 1.008 | 1.004 | 1.006 | 0.998 | 0.999 | 1.020 | 1.001 |
| dE/dR | 0.735 | 0.799 | 0.721 | 0.795 | 0.821 | 0.889 | 0.739 | 0.909 |
| Clarity, (1) | | | | | | | | |
| Extract | 2 | 2 | 1 | 3 | 2 | 3 | 3 | 3 |
| Raffinate | 1 | 1 | 1 | 1 | 1 | 1 | 4 | 1 |

(1) 1 = Clear, 2 = Translucent, 3 = Heavy Haze, and 4 = opaque

The single-stage extractions indicated that toluene, LUF, and HUF had the highest and most favorable dimethyl carbonate Distribution Coefficients, calculated as the weight percent of dimethyl carbonate in the extract divided by the weight percent of dimethyl carbonate in the raffinate. The LCN and TCN has slightly lower dimethyl carbonate Distribution Coefficient. While not wishing to be bound to any particular theories, this may be attributed in part to the substantially higher aromaticity of the toluene and light and heavy reformate products.

A subjective clarity test was performed on the extract and raffinate phases as a further indication of projected solvent extraction performance. The raffinate phase, comprising in excess of 90 weight percent water for all cases, was generally clear except for the alkylate solvent case. The extract phase clarity ranged from clear to a heavy haze. The best solvents with regard to extract clarity were the LCN followed by the LUF, LVN, and HVN. While not wishing to be bound to any particular theories, the LCN may have had the best extract clarity because of its effect on the density disparity between the extract and raffinate phases as reflected in the ratio of extract density to raffinate density. The heavier aromatic extraction solvents HUF and toluene appeared hazy. This result may be related, in part, to the small density disparity in extract and raffinate phases when toluene and HUF were the extraction solvents. This Example illustrates that the best solvents selective for extracting alkyl carbonate from streams comprising alkyl carbonate and water and LUF and LCN followed by the group of toluene, HUF, and LVN.

EXAMPLE 2

An experimental laboratory simulation of a three-stage "stripping only" countercurrent extraction was conducted in a manner similar to that described in Example 1. The testing approach is described in *Mass Transfer Operations by Treybal*, pages 518-520, 3rd Edition, 1980.

The method utilizes well-shaken separator funnels which generally approach one hundred percent stage efficiency. Therefore, for purposes of the present invention, the number of stages, or for this study, one theoretical stage refers to a theoretical stage which approximates the separation which can be obtained from a well-shaken separator funnel. Mechanical stages, such as the number of trays in a trayed extraction column or the height of packing in a packed extraction column can be estimated using established techniques to account for stream compositions, process variables, and mechanical design.

Approximately 22.0 grams of a feedstock comprising about 82 weight percent dimethyl carbonate and 18 weight percent water was directed to an extraction step using 44.0 grams as catalytic reformate as the alkyl carbonate extraction solvent. The catalytic reformate used as the alkyl carbonate extraction solvent was stabilized catalytic reformate wherein a substantial portion of the pentane and lighter hydrocarbon components were removed from the product. Other than this stabilization step, full range reformate was used as the extraction solvent.

The liquid-liquid extraction column was operated with 3 theoretical stages of stripping extraction which simulates the injection of an alkyl carbonate-containing feedstock into the top of a liquid-liquid extraction column having 3 theoretical stages of stripping extraction below the feedstock inlet. The composition and weight of the extract and raffinate streams derived from this test are provided in Table 3. A tabulation of the stage-by stage composition profiles is provided in Table 4.

TABLE 3

| Balances, wt, wt % | Wt. gms | Wt % |
|---|---|---|
| Feed | | |
| DMC | 18.0 | 82.0 |
| Water | 4.0 | 18.0 |
| Reformate | 44.0 | |
| Total | 66.0 | 100.0 |
| Products | | |
| Extract | | |
| DMC (DEC) | 17.1 | 28.6 |
| Water | 0.0 | 0.0 |
| Reformate | 42.7 | 71.4 |
| Total | 59.8 | 100.0 |
| Raffinate | | |
| DMC (DEC) | 0.0 | 0.0 |
| Water | 3.8 | 99.9 |
| Reformate | 0.0 | 0.1 |
| Total | 3.8 | 100.0 |
| Weight Balance | 96.4 | |
| Wt % DMC in Feed Recovered to Extract | 95.0 | |
| Wt % Water in Feed Recovered to Raffinate | 95.0 | |

TABLE 4

| Liquid Phase | Component | F Feed (g/cc) | 2 Strip. (g/cc) | 3 Strip. (g/cc) |
|---|---|---|---|---|
| Extract | DMC | 0.240 | 0.008 | 0.003 |
| Extract | Water | 0.000 | 0.000 | 0.000 |
| Raffinate | DMC | 0.058 | 0.002 | 0.000 |
| Raffinate | Water | 0.882 | 0.936 | 0.929 |

☐ Denotes Product Streams

Table 3 illustrates that the three-stage "stripping-only" liquid-liquid extraction process of Example 2 provided recovery of 95 percent of the dimethyl carbonate to the extract product. Moreover, this recovery may actually be higher in view of the 96.4 percent weight balance. The process also provided an extract product having de minimus water. It is apparent that a rectification section is not necessary for practice of the present invention. However, in an industrial environment, it is anticipated that water may carryover to a location above the feedstock inlet of a liquid-liquid extraction column and therefore, a rectification section could prove beneficial.

Table 3 also illustrates that 95 percent of the water present in the liquid-liquid extraction step feedstock was recovered to the raffinate product. This figure may also have been underestimated in view of the 96.4 percent weight balance. The raffinate product contained less than 0.01 weight percent dimethyl carbonate, less than 0.1 weight percent reformate, and over 99.9 weight percent water.

Table 4 illustrates that a great degree of the extraction is performed in stripping stages 1 and 2. This indicates that at bench scale and with reformate as the liquid-liquid hydrocarbon extraction solvent, as little as 2 or even 1 theoretical stage of stripping extraction can provide superior extraction performance.

Other embodiments of the invention will be apparent to those skilled in the art from a consideration of this specification or from practice of the invention disclosed herein. It is intended that this specification be considered as exemplary only with the true scope and spirit of the invention being indicated by the following claims.

That which is claimed is:

1. A process for separating alkyl carbonate from a feedstock comprising at least one alkyl carbonate and at least 0.01 percent by weight water comprising extracting said alkyl carbonate from said feedstock in a liquid-liquid extraction step comprising an extraction solvent selective for extracting alkyl carbonates relative to water in an amount sufficient to extract a substantial amount of said alkyl carbonates from said feedstock, said extraction solvent substantially comprising hydrocarbon boiling at a temperature ranging from about 50° F. to about 700° F. at atmospheric pressure and having a specific gravity ranging from about 0.50 to about 1.00.

2. The process of claim 1 wherein said alkyl radical of said alkyl carbonate has less than 9 carbon atoms and said extraction solvent substantially comprises hydrocarbon boiling at a temperature ranging from about 50° F. to about 450° F. at atmospheric pressure.

3. The process of claim 1 wherein said alkyl radical of said alkyl carbonate has from 6 to 20 carbon atoms and said extraction solvent substantially comprises hydrocarbon boiling at a temperature ranging from about 250° F. to about 700° F. at atmospheric pressure.

4. The process of claim 2 wherein said extraction solvent comprises one or more nonpolar hydrocarbon streams selected from the group consisting of fluid catalytic cracking unit naphtha, coker naphtha, light virgin naphtha, heavy virgin naphtha, hydrocracker naphtha, resid hydroprocessor naphtha, catalytic reformate, alkylate, isomerate, benzene, toluene, xylene, and combinations thereof.

5. The process of claim 2 wherein said extraction solvent comprises at least 1.0 percent by weight aromatic hydrocarbon and less than 80.0 percent by weight olefinic hydrocarbon.

6. The process of claim 2 wherein said extraction solvent comprises from about 5.0 to about 50.0 percent by weight aromatic hydrocarbon and less than 80.0 percent by weight olefinic hydrocarbon.

7. The process of claim 1 wherein said liquid-liquid extraction step is conducted in a liquid-liquid extraction column at a temperature ranging from about 32° F. to about 150° F. and a pressure ranging from about 0 psig to about 100 psig for producing an overhead product comprising a substantial amount of said alkyl carbonate and a bottoms product comprising less than 15.0 percent by weight of alkyl carbonate.

8. The process of claim 7 wherein the weight ratio of said extraction solvent to alkyl carbonate in said feedstock ranges from about 30:1 to about 1:1 and at least 75 percent of said alkyl carbonate present in said feedstock is recovered to said overhead product.

9. A process for separating alkyl carbonate from a feedstock comprising at least one alkyl carbonate, at least one alkanol, and at least 0.10 percent by weight water comprising:

fractionating by distillation said feedstock into an overhead product comprising a substantial fraction of alkanol and alkyl carbonate and a bottoms product comprising alkyl carbonate and water; and extracting alkyl carbonate from said bottoms product comprising alkyl carbonate and water in a liquid-liquid extraction step comprising an extraction solvent selective for extracting alkyl carbonate relative to water in an amount sufficient to extract a substantial amount of said alkyl carbonate from said feedstock, said extraction solvent comprising substantially hydrocarbon boiling at a temperature ranging from about 50° F. to about 700° F. at atmospheric pressure and having a specific gravity ranging from about 0.60 to about 1.00.

10. The process of claim 9 wherein said alkyl radical of said alkyl carbonate has less than 9 carbon atoms and said extraction solvent substantially comprises hydrocarbon boiling at a temperature ranging from about 50° F. to about 450° F. at atmospheric pressure.

11. The process of claim 10 wherein said extraction solvent comprises from about 5.0 to about 50.0 percent by weight aromatic hydrocarbon and less than 80.0 percent by weight olefinic hydrocarbon.

12. The process of claim 10 wherein said liquid-liquid extraction step is conducted in a liquid-liquid extraction column at a temperature ranging from about 32° F. to about 120° F. and a pressure ranging from about 0 psig to about 75 psig for producing an overhead product comprising a substantial amount of said alkyl carbonate and a bottoms product comprising less than 15.0 percent by weight of alkyl carbonate.

13. The process of claim 10 wherein the weight ratio of said extraction solvent to alkyl carbonate in said feedstock ranges from about 10:1 to about 3:1 and at least 75 percent of said alkyl carbonate present in said feedstock is recovered to said overhead product.

14. The process of claim 12 wherein at least a portion of said overhead product comprising a substantial amount of said alkyl carbonate is processed into gasoline.

15. A process for separating alkyl carbonate from a feedstock comprising at least one alkyl carbonate, at least one alkanol, and at least 0.10 percent by weight water comprising:

fractionating said feedstock by distillation extraction into an overhead product comprising alkyl carbonate and water and a bottoms product comprising a substantial fraction of alkanol and water utilizing an extractive distillation solvent selective for extracting alkanol relative to alkyl carbonate comprising water in an amount sufficient to separate a substantial fraction of said alkanol from said feedstock; and extracting alkyl carbonate from said overhead product comprising alkyl carbonate and water in a liquid-liquid extraction step comprising an extraction solvent selective for extracting alkyl carbonate relative to water in an amount sufficient to extract a substantial amount of said alkyl carbonate from said feedstock, said extraction solvent comprising substantially hydrocarbon boiling at a temperature ranging from about 50° F. to about 700° F. at atmospheric pressure and having a specific gravity ranging from about 0.60 to about 1.00.

16. The process of claim 15 wherein said alkyl radical of said alkyl carbonate has less than 9 carbon atoms and said extraction solvent substantially comprises hydrocarbon boiling at a temperature ranging from about 50° F. to about 450° F. at atmospheric pressure.

17. The process of claim 15 wherein said extraction solvent comprises one or more nonpolar hydrocarbon streams selected from the group consisting of fluid catalytic cracking unit naphtha, light virgin naphtha, catalytic reformate, benzene, toluene, and combinations thereof.

18. The process of claim 15 wherein said extraction solvent comprises from about 5.0 to about 50.0 percent by weight aromatic hydrocarbon and less than 80.0 percent by weight olefinic hydrocarbon.

19. The process of claim 15 wherein said liquid-liquid extraction step is conducted in a liquid-liquid extraction column at a temperature ranging from about 32° F. to about 100° F. and a pressure ranging from about 0 psig to about 50 psig for producing an overhead product comprising a substantial amount of said alkyl carbonate and a bottoms product comprising less than 15.0 percent by weight of alkyl carbonate.

20. The process of claim 19 wherein at least a portion of said overhead product comprising a substantial amount of said alkyl carbonate is processed into gasoline and at least a portion of said bottoms product comprising less than 15.0 percent by weight of alkyl carbonate is directed back to said fractionating step.

* * * * *